(12) United States Patent
Inoue et al.

(10) Patent No.: US 11,571,535 B2
(45) Date of Patent: Feb. 7, 2023

(54) WEARABLE DEVICE AND PROGRAM

(71) Applicants: OMRON Corporation, Kyoto (JP); OMRON HEALTHCARE CO., LTD., Kyoto (JP)

(72) Inventors: Kosuke Inoue, Kyoto (JP); Shusuke Eshita, Kyoto (JP)

(73) Assignee: Omron Corporation, Kyoto (JP)

( * ) Notice: Subject to any disclaimer, the term of this patent is extended or adjusted under 35 U.S.C. 154(b) by 672 days.

(21) Appl. No.: 16/609,654

(22) PCT Filed: May 1, 2018

(86) PCT No.: PCT/JP2018/017367
§ 371 (c)(1),
(2) Date: Oct. 30, 2019

(87) PCT Pub. No.: WO2018/211965
PCT Pub. Date: Nov. 22, 2018

(65) Prior Publication Data
US 2020/0061316 A1    Feb. 27, 2020

(30) Foreign Application Priority Data
May 15, 2017  (JP) .............................. JP2017-096681

(51) Int. Cl.
*A61M 16/00* (2006.01)
*A61B 5/0205* (2006.01)
(Continued)

(52) U.S. Cl.
CPC ......... *A61M 16/0051* (2013.01); *A61B 5/021* (2013.01); *A61B 5/02055* (2013.01);
(Continued)

(58) Field of Classification Search
CPC .............. A61M 16/0051; A61M 16/06; A61M 2205/582; A61M 2230/30; A61B 5/021; A61B 5/4818; A61B 2560/0276
See application file for complete search history.

(56) References Cited

U.S. PATENT DOCUMENTS 6,349,724 B1   2/2002 Burton et al.
2003/0236452 A1  12/2003 Melker et al.
(Continued)

FOREIGN PATENT DOCUMENTS

JP   H11-314903 A   11/1999
JP   2004-500969 A   1/2004
(Continued)

OTHER PUBLICATIONS

Dimsdale et al., Effect of Continuous Positive Airway Pressure on Blood Pressure: A Placebo Trial, Jan. 2000, Hypertension: Effect of CPAP on Blood Pressure, pp. 144-147 (Year: 2000).*

(Continued)

*Primary Examiner* — Toan M Le
(74) *Attorney, Agent, or Firm* — Osha Bergman Watanabe & Burton LLP

(57) ABSTRACT

A wearable device includes a blood pressure sensor configured to continuously measure blood pressure of a measurement subject; a check section configured to, in response to an instruction for commencing a continuous measurement of the blood pressure, check whether a treatment device to be used during the continuous measurement of the blood pressure is attached to the measurement subject; a measurement controller configured to, when the check section confirms that the treatment device is attached, execute a continuous measurement of the blood pressure with the blood pressure sensor; and a display section configured to, when the check section does not confirm that the treatment device is attached, display a form of guidance to prompt attachment of the treatment device.

15 Claims, 8 Drawing Sheets

(51) Int. Cl.
    *A61M 16/06*      (2006.01)
    *A61B 5/021*      (2006.01)
    *A61B 5/00*      (2006.01)

(52) U.S. Cl.
    CPC .......... *A61M 16/024* (2017.08); *A61M 16/06* (2013.01); *A61B 5/4818* (2013.01); *A61B 2560/0276* (2013.01); *A61M 2205/582* (2013.01); *A61M 2230/30* (2013.01)

(56) References Cited

U.S. PATENT DOCUMENTS

2005/0076906 A1    4/2005    Johnson
2012/0125337 A1    5/2012    Asanoi

FOREIGN PATENT DOCUMENTS

JP      2005-529713 A    10/2005
JP      2014-180411 A    9/2014
WO    2011/019091 A1    2/2011

OTHER PUBLICATIONS

English Translation of the International Preliminary Report on Patentability for International Application No. PCT/JP2018/017367, dated Nov. 21, 2019 (5 pages).
International Search Report issued in Application No. PCT/JP2018/017367, dated Jun. 19, 2018 (5 pages).
Written Opinion issued in Application No. PCT/JP2018/017367, dated Jun. 19, 2018 (10 pages).
Office Action issued in the counterpart Chinese Patent Application No. 201880030433.8, dated Nov. 11, 2021 (24 pages).

* cited by examiner

WEARABLE DEVICE AND PROGRAM

This is a U.S. national phase application under 35 USC 371 of International Application PCT/JP2018/017367 (not published in English), filed May 1, 2018.

FIELD

The present invention relates to a wearable device for measuring the blood pressure of a measurement subject and a program therefor.

BACKGROUND

Continuous positive airway pressure (CPAP) is commonly known as a conventional treatment for sleep apnea syndrome (SAS). CPAP is a treatment for prevention of apnea during sleep by sending pressurized air from a mask attached to the nose into the airway and widening the airway (for example, Jpn. Pat. Appln. KOKAI Publication No. 2014-180411). If the apneic state continues, the blood oxygen level may be lowered, which may lead to considerable fluctuations of the blood pressure. If the SAS-caused fluctuations of the blood pressure increase during sleep, the risk of developing cerebro/cardio-vascular events increases. This means that, by treating the SAS or SAS-related fluctuations in blood pressure, the risk of developing cerebro/cardio-vascular events can be reduced.

SUMMARY

The CPAP treatment of the SAS is predicated on the proper functioning of the CPAP machine. If the mask of the CPAP machine is, for example, improperly attached, the alleviation of the SAS condition cannot be expected. In most cases, a CPAP machine is worn by the user him/herself, and operated by his/her own manipulation. In the CPAP treatment of the SAS, the reliability of the user's operation, such as attachment of the mask, raises issues. In addition, since the CPAP machine is employed during sleep, for example, for the treatment of SAS, it is difficult to prompt the user to put the mask on him/herself once the onset of sleep begins.

The present invention has been conceived in light of the above circumstances. The purpose of the present invention is to provide a wearable device and a program capable of urging a user to reliably attach the treatment device.

To address the above issue, the wearable device according to the first aspect of the present invention includes a blood pressure sensor configured to continuously measure blood pressure of a measurement subject; a check section configured to, in response to an instruction for commencing a continuous measurement of the blood pressure, check whether a treatment device to be used during the continuous measurement of the blood pressure is attached to the measurement subject; a measurement controller configured to, when the check section confirms that the treatment device is attached, execute a continuous measurement of the blood pressure with the blood pressure sensor; and a display section configured to, when the check section does not confirm that the treatment device is attached, display a form of guidance to prompt attachment of the treatment device.

In the first aspect, the treatment device of the wearable device according to the second aspect of the present invention is a CPAP machine.

In the first or second aspect, the wearable device according to the third aspect of the present invention further includes a vibrator configured to, when the check section does not confirm that the treatment device is attached, vibrate a main body of the wearable device.

In any one of the first, second, and third aspect, the measurement controller of the wearable device according to the fourth aspect of the present invention satisfies a predetermined condition during the continuous measurement of the blood pressure of the measurement subject, the check section checks whether the treatment device is attached to the measurement subject.

In any one of the first, second, third, and fourth aspect, the blood pressure sensor of the wearable device according to the fifth aspect of the present invention includes a sensor of a PTT system, a tonometry system, an optical system, a radio wave system, or an ultrasonic system.

According to the first aspect of the present invention, whether the treatment device is attached can be checked when commencing the continuous measurement of the blood pressure, and the measurement subject can be prompted to reliably attach the treatment device to him/herself.

According to the second aspect of the present invention, when commencing the continuous measurement of the blood pressure that is suspected to be of relevance to the sleep apnea syndrome, the measurement subject can be prompted to reliably wear a CPAP machine for treating the sleep apnea syndrome so that the blood pressure data that possibly provides information for verifying the effects of the CPAP machine can be reliably acquired.

According to the third aspect of the present invention, the CPAP machine or any other treatment device being unattached can be signaled not only by virtue of a display, but also by virtue of vibrations of the main body of the wearable device attached to the measurement subject.

According to the fourth aspect of the present invention, whether the CPAP machine or any other treatment device is attached can be checked even during the continuous measurement of the blood pressure, and a notice can be sent to the measurement subject, for example, when the treatment device has become detached during the continuous measurement of the blood pressure.

According to the fifth aspect of the present invention, the blood pressure sensor for continuously measuring the blood pressure is not limited to a specific form, and the measurement subject can be prompted to wear the treatment device in a reliable fashion even during the continuous measurement of the blood pressure of various forms.

DETAILED DESCRIPTION

Embodiments according to the present invention will be described below with reference to the drawings.

Figure 1:
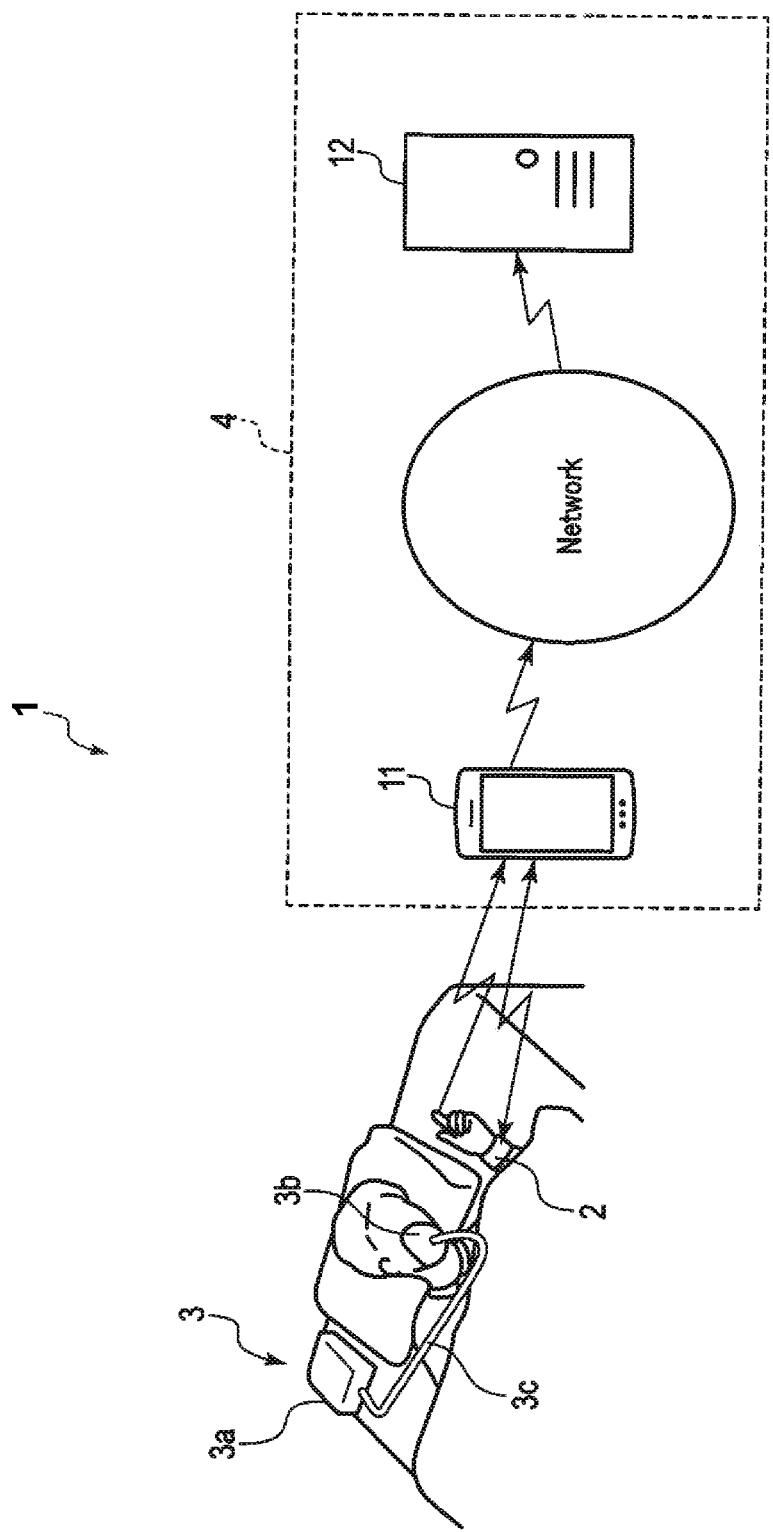
FIG. 1 is a diagram schematically showing an exemplary structure of a treatment system according to an embodiment of the present invention.

FIG. 1 is a diagram schematically showing an exemplary structure of a treatment system according to an embodiment.

A treatment system 1 includes a wearable device (blood pressure measurement device) 2, a CPAP machine (treatment device) 3, and an information processing system (information processing device) 4. The information processing system 4 is a data processing system that includes devices communicable with the wearable device 2 and the CPAP machine 3. In the exemplary structure of FIG. 1, the information processing system 4 includes a user terminal 11 and a server 12. The information processing system 4 obtains measurement data including blood pressure data and various other types of measurement data that are continuously measured by the wearable device 2, and analyzes the obtained measurement data.

In the exemplary structure of FIG. 1, the wearable device 2 and the CPAP machine 3 are connected to the user terminal 11, and the user terminal 11 is connected to the server 12 via the network in a communicable manner. However, the structures of the treatment system 1 and information processing system 4 are not limited to that shown in FIG. 1. For example, part or all of the functions (processing) realized by the server 12, which will be described later, may be performed by the user terminal 11. Part or all of the functions of the user terminal 11 and the server 12, which will be described later, may also be performed by the wearable device 2.

In other words, the information processing device that serves as the information processing system 4 may be realized by the user terminal 11, with the server 12 omitted. If this is the case, the entire operation of the information processing system 4, which will be described later, and the operation of the server 12 may be realized by the user terminal 11. The CPAP machine 3 may be connected to the wearable device 2, instead of being connected to the user terminal 11. If this is the case, the CPAP machine 3 may be configured to communicate with the user terminal 11 or the server 12 via the wearable device 2. Furthermore, the functions of the information processing system 4 may be realized by the wearable device 2. If this is the case, with the CPAP machine 3 connected to communicate with the wearable device 2, the user terminal 11 and the server 12 may be omitted, and the treatment system described in this embodiment can therefore be constituted by the wearable device 2 and the CPAP machine 3.

The wearable device 2 is a blood pressure measurement device having at least a function of continuously measuring a blood pressure value of a measurement subject (user). The wearable device 2 is not limited to continuously measuring the blood pressure value of the user; the wearable device 2 is also provided with a function of measuring biological data such as the amount of activity, the number of steps taken, and sleep conditions, and environmental data such as temperature and humidity. The wearable device 2 is also a computer that can perform data processing by application programs stored in a memory. The wearable device 2 may have a structure such as a wristwatch that the user can wear.

The CPAP machine 3 is a treatment device that is attached to the user having a case of sleep apnea syndrome (SAS), during sleep. The CPAP machine 3 sends pressurized air from a mask attached to the user's nose into the airway, and widens the airway to prevent apnea during the sleep. In this embodiment, the CPAP machine 3 is a treatment device that is attached during a period of time in which the wearable device 2 is continuously measuring the blood pressure values (i.e., during monitoring).

In the exemplary structure shown in FIG. 1, the CPAP machine 3 has a machine main body 3a, a mask 3b, and a tube 3c. The machine main body 3a and mask 3b are connected to each other via the tube 3c. The mask 3b is attached to the user's nose. The machine main body 3a is placed within a range where the mask 3b connected thereto via the tube 3c can stay attached to the user's nose during the sleep. The machine main body 3a sends pressurized air into the tube 3c. The air from the machine main body 3a is supplied to the mask 3b through the tube 3c. The mask 3b sends the pressured air supplied through the tube 3c, through the nostrils to the user's airway.

In this embodiment, the CPAP machine 3 has a function of making a communicable connection to the user terminal 11, and is configured to transmit information indicating the operation status to the user terminal 11. For example, the machine main body 3a of the CPAP machine 3 detects whether the mask 3b is properly attached to the user, for example, based on a signal detected by a sensor provided in the mask 3b. The machine main body 3a may detect the state of attachment to the user in accordance with magnetic field electrodes provided in the mask 3b. The machine main body 3a may also detect the attachment state of the mask 3b based on signals detected by an atmospheric pressure sensor and a flow rate sensor.

The machine main body 3a supplies a signal indicating the attachment state of the mask 3b to the user terminal 11. Based on the signal from the machine main body 3a, the user terminal 11, or the wearable device 2 or the server 12 connected to the machine main body 3a via the user terminal 11, can detect whether the CPAP machine 3 is properly attached to the user. Furthermore, the machine main body 3a of the CPAP machine 3 and the wearable device 2 may acquire information indicating the attachment state of the mask 3b to the user, based on mutual sensing of the magnetic field electrodes provided in the mask 3b.

The user terminal 11 is an information communication terminal used by an individual user. The user terminal 11 is a portable information communication terminal such as a smartphone, a mobile phone, a tablet PC, or a notebook PC. The user terminal 11 will suffice as long as it is provided at least with a function of communicating with the wearable device 2 and the CPAP machine 3.

The server 12 is provided with a function of communicating with the user terminal 11. In the exemplary structure of FIG. 1, it is assumed that the server 12 communicates with the user terminal 11 via a network. The server 12 will suffice as long as it can communicate with the user terminal 11, and its communication system or scheme is not limited to a specific one. The server 12 acquires data from the wearable device 2 and the CPAP machine 3 via the user terminal 11.

Figure 2:
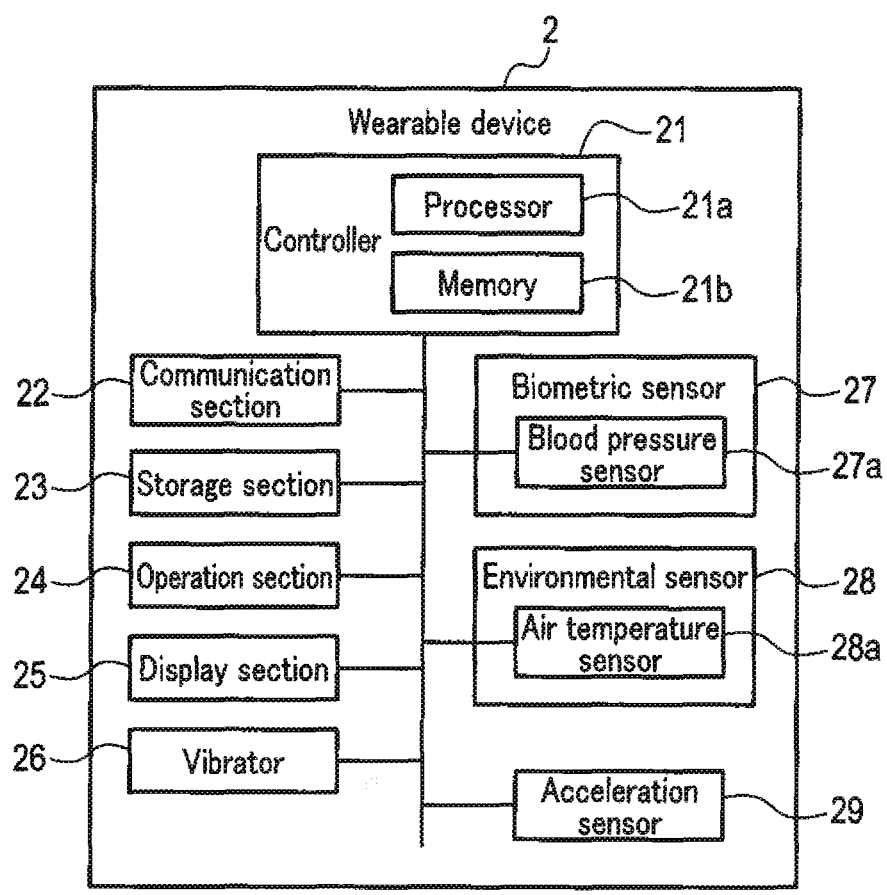
FIG. 2 is a block diagram showing an exemplary structure of a wearable device.

FIG. 2 is a block diagram showing an exemplary structure of the wearable device 2 shown in FIG. 1.

The wearable device 2 includes a controller 21, a communication section 22, a storage section 23, an operation section 24, a display section 25, a vibrator 26, a biometric sensor 27, an environmental sensor 28, and an acceleration sensor 29.

The controller 21 includes at least one processor 21a and memory 21b. With the processor 21a executing programs by using the memory 21b, the controller 21 implements various types of operation control and data processing. The processor 21a may be a central processing unit (CPU) or a microprocessing unit (MPU) that includes an arithmetic circuit. The memory 21b includes a non-volatile memory that stores programs to be executed by the processor 21a, and a memory such as a RAM that is used as a work memory. The controller 21 includes a clock (not shown) and a clock function for measuring the current date and time.

In the controller 21, the processor 21a executes a program stored in the memory 21b or the storage section 23, and thereby executes control and data processing of individual components. That is, the processor 21a controls the operations of individual components according to an operation signal from the operation section 24, and performs data processing on the measurement data measured by the biometric sensor 27 and the environmental sensor 28. For example, the controller 21 executes the operation in a mode (monitoring mode) of continuously measuring the blood pressure value of the measurement subject in response to an instruction from the operation section 24, and transmitting the continuously measured blood pressure data (hereinafter referred to as "blood pressure data") to the user terminal 11 or server 12.

The communication section 22 is a communication interface for communicating with the user terminal 11. The communication section 22 transmits data to the user terminal 11 and receives data from the user terminal 11. The communication performed by the communication section 22 may be either wireless communication or wired communication. In this embodiment, the communication section 22 is described as communicating with the user terminal 11 by near field communication, but the communication section 22 is not limited to this. The communication may be performed using a communication cable, or via a network such as a local area network (LAN).

The storage section 23 stores program data for controlling the wearable device 2, setting data for setting various functions of the wearable device 2, measurement data measured by the biometric sensor 27, environmental sensor 28, and acceleration sensor 29, and the like. The storage section 23 may be used as a work memory for executing a program.

The operation section 24 is constituted by operation devices such as a touch panel and operation buttons (operation keys). The operation section 24 detects an operation by the user (measurement subject), and outputs an operation signal describing the operation to the controller 21. The operation section 24 is not limited to the touch panel and operation buttons. The operation section 24 may be provided with a voice recognition section that recognizes the instructions for the operation by the user's voice, a biometric authentication section that authenticates part of the user's body, an image recognition section that recognizes the user's facial expression and gestures from the images of the user's face and body, and the like.

The display section 25 includes, for example, a display screen (e.g., a liquid crystal display (LCD) or an electroluminescence (EL) display) and an indicator; and the display section 25 displays information according to a control signal from the controller 21. In the present embodiment, the operation section 24 and the display section 25 are described as being constituted by a display device having a touch panel.

The vibrator 26 vibrates the main body of the wearable device 2. The vibrator 26 is constituted, for example, by a motor and a weight that is decentered from the rotational center of the rotation axis of the motor. With such a structure, the vibrator 26 generates vibrations by rotating the motor in response to a control instruction from the controller 21.

The biometric sensor 27 measures the user's biometric information, and outputs the biometric data that is the measurement data of the biometric information. The biometric sensor 27 includes a sensor for detecting signals indicating various biometric information values such as blood pressure, in contact with, or in the vicinity of, part of the body of the measurement subject. The biometric sensor 27 may be configured, for example, as a band, so as to be arranged in contact with, or in the vicinity of, a predetermined position of the measurement subject. The controller 21 acquires various types of biometric data output from the biometric sensor 27, as the biometric data associated with the measurement time that is set with reference to the time information. The biometric sensor 27 includes at least a blood pressure sensor 27a. The blood pressure sensor 27a continuously measures the user's blood pressure value to acquire blood pressure data as the biometric data.

In addition to the blood pressure data, the biometric data acquired by the biometric sensor 27 may include pulse wave data, pulse data, electrocardiogram data, heart rate data, and body temperature data. The sensors for measuring these types of biometric data may be provided as a biometric sensor 27. These types of biological data may be output as components of the measurement data other than the blood pressure. For example, the electroencephalogram data can be adopted as measurement data indicating a human sleeping state.

The blood pressure sensor 27a is a blood pressure sensor of a continuous measurement type. The blood pressure sensor 27a is a blood pressure sensor that can continuously measure the value of blood pressure (e.g., systolic and diastolic blood pressures). The blood pressure sensor 27a may include, but is not limited to, a blood pressure sensor that can continuously measure the blood pressure for every beat.

A blood pressure sensor of continuous measurement type using a PTT system, a tonometry system, an optical system, a radio wave system, or an ultrasonic system may be adopted as the blood pressure sensor 27a. The PTT system measures pulse transmit time (PTT) and estimates the blood pressure value based on the measured pulse transmit time. In the tonometry system, the blood pressure value is measured by using information detected by the pressure sensor, which is brought into direct contact with a site of the body where an artery such as the radial artery in the wrist runs. In the optical system, radio wave system, and ultrasonic system, light, radio waves, or ultrasonic waves are applied to the blood vessels, and blood pressure values are measured from the reflected waves.

The blood pressure sensor of continuous measurement type can measure the user's blood pressure waveform, obtain the blood pressure value based on the measured blood pressure waveform, and calculate the heart rate based on the cycle of the measured blood pressure waveform. The heart rate data may include, but is not limited to, a heart rate. The heart rate is not limited to the measurement by a blood pressure sensor of a continuous measurement type, but may be measured by a heart rate sensor.

The environmental sensor 28 includes a sensor that measures environmental information around the user and obtains the measured environmental data. In the exemplary structure shown in FIG. 2, the environmental sensor 28 includes an air temperature sensor 28a. In addition to a sensor for air temperature, the environmental sensor 28 may also include sensors for measuring temperature, humidity, sound, light, and the like. The environmental sensor 28 will suffice as long as it includes a sensor that measures environmental information (environmental data) that can be expected to have a direct or indirect relationship with fluctuations of blood pressure values. The controller 21 acquires environmental data measured by the environmental sensor 28, as measurement data (environmental data) associated with the measurement time that is set with reference to the time information.

The acceleration sensor 29 detects the acceleration received by the main body of the wearable device 2. For example, the acceleration sensor may acquire 3-axis or 6-axis acceleration data. The acceleration data may be used for estimating the amount of activity (posture and/or movement) of the user who is wearing the wearable device 2.

For example, if the user is sleeping, the change in the posture of the measurement subject, which is estimated from the acceleration data measured by the acceleration sensor 29, can be the data indicating the sleeping state (depth of sleep) of the measurement subject. If this is the case, the controller 21 associates the measurement time with the acceleration data measured by the acceleration sensor 29, and outputs the data as sleeping state measurement data.

Also, if the user is awake, the change in the motion estimated from the acceleration data can take the form of data indicating the amount of user's activity (e.g., the amount of activity during exercise such as walking or jogging). If this is the case, the controller 21 associates the measurement time with the acceleration data measured by the acceleration sensor 29, and outputs the data as activity measurement data.

The user's wakened state may be detected by the user's movement detected by the acceleration sensor 29. Alternatively, the wakened state may be determined in accordance with the user's operation. For example, the user may indicate by way of the operation section 24 that he/she is going to bed immediately before bedtime, or that he/she is awakened immediately after waking.

Next, the structure of the user terminal 11 will be described.

Figure 3:
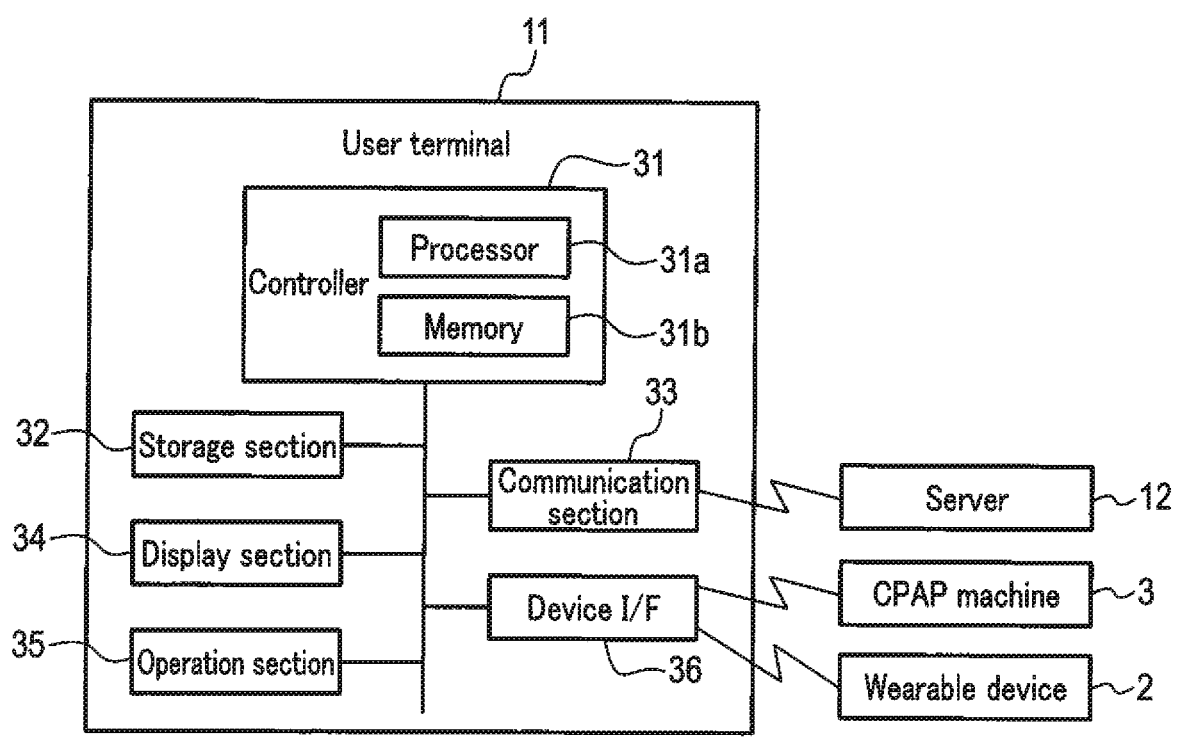
FIG. 3 is a block diagram showing an exemplary structure of a user terminal.

FIG. 3 is a block diagram showing an exemplary structure of the user terminal 11 of FIG. 1.

In the exemplary structure shown in FIG. 3, the user terminal 11 includes a controller 31, a storage section 32, a communication section 33, a display section 34, an operation section 35, a device interface (I/F) 36, and the like. In the present embodiment, the user terminal 11 is a mobile communication terminal such as a smartphone or a tablet, in which application software (program) is installed to implement the processing that is described later.

The controller 31 has at least one processor 31a and memory 31b. With the processor 31a executing programs by using the memory 31b, the controller 31 implements various types of operation control and data processing. The processor 31a may be a CPU or MPU that includes an arithmetic circuit. The memory 31b includes a non-volatile memory that stores programs to be executed by the processor 31a, and a volatile memory such as a RAM that is used as a work memory. The controller 31 includes a clock (not shown) and a clock function for measuring the current date and time.

The storage section 32 is a data memory. The storage section 32 may be constituted by a semiconductor memory (memory card or solid state drive (SSD)) or a magnetic disk (hard disk (HD)). The storage section 32 may store programs to be executed by the processor 31a of the controller 31. The storage section 32 may store data supplied from the wearable device 2 and the CPAP machine 3. The storage section 32 may also store display data that is to be displayed on the display section 34.

The communication section 33 is a communication interface for communicating with the server 12. The communication section 33 transmits data to the server 12 and receives data from the server 12 via the network. The communications performed by the communication section 33 may be wireless communication or wired communication. In the present embodiment, the network will be described as, but not limited to, the Internet. The network may be of any other type such as LAN, or one-to-one communication may be performed using a communication cable such as USB cable.

The display section 34 includes a display screen (e.g., LCD or EL display). The display section 34 is under the control of the controller 31 so that the contents displayed on the display screen are controlled.

The operation section 35 transmits an operation signal corresponding to the operation by the user (measurement subject) to the controller 31. The operation section 35 may be a touch panel provided on the display screen of the display section 34. The operation section 35 is not limited to the touch panel, and may include operation buttons, a keyboard, a mouse, or the like. The operation section 35 may be provided with a voice recognition section that recognizes the instructions for an operation by the user's voice, a biometric authentication section that authenticates part of the user's body, an image recognition section that recognizes the user's facial expression and gestures, and the like.

The device I/F 36 is a communication interface for communicating with the wearable device 2 and the CPAP machine 3. The device I/F 36 receives data from the wearable device 2 and the CPAP machine 3, and transmits an operation instruction to the wearable device 2 and the CPAP machine 3. The device I/F 36 may include an interface for the wearable device 2 and an interface for the CPAP machine 3. The communications performed by the device I/F 36 may be wireless communication or wired communication.

In the present embodiment, the device I/F 36 is described as having a configuration of communicating with the wearable device 2 and the CPAP machine 3 by near field communications (e.g., Bluetooth (trademark)), but is not limited thereto. The wearable device 2 or CPAP machine 3 may include an interface for realizing communications via a communication cable. The device I/F 36 may realize serial communications via a communication cable, or via a network such as a LAN.

In this embodiment, it is assumed that the CPAP machine 3 that can communicate via the device I/F 36 supplies information indicating the attachment state of the mask 3b to the user terminal 11. The CPAP machine 3 may also supply to the user terminal 11 the data indicating the breathing state of the user detected by the atmospheric pressure sensor, a flow rate sensor, or the like.

Next, the configuration of the server 12 will be described.

Figure 4:
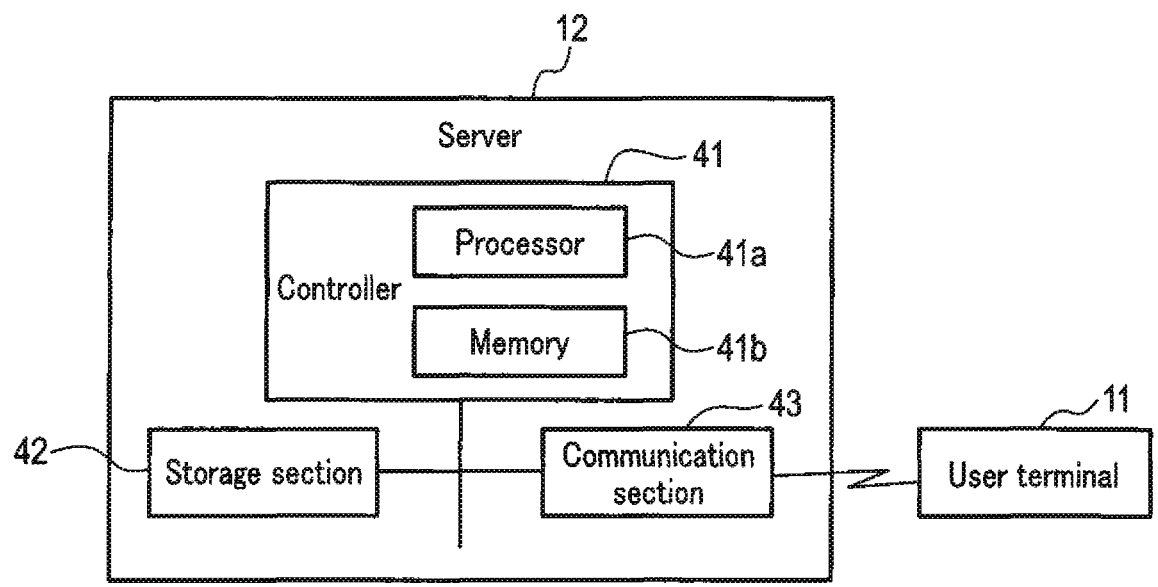
FIG. 4 is a block diagram showing an exemplary structure of a server.

FIG. 4 is a block diagram showing an exemplary structure of the server 12 shown in FIG. 1.

The server 12 includes a controller 41, a storage section 42, and a communication section 43. In the present embodiment, the server 12 will be described as a general-purpose computer device in which a program (software) is installed to implement the processing that is described later.

The controller 41 has at least one processor 41a and memory 41b. With the processor 41a executing programs by using the memory 41b, the controller 41 implements various types of operation control and data processing. The processor 41a may be a CPU or MPU that includes an arithmetic circuit. The memory 41b includes a non-volatile memory that stores programs to be executed by the processor 41a, and a volatile memory such as a RAM that is used as a work memory. The controller 41 includes a clock (not shown) and a clock function for measuring the current date and time.

The storage section 42 is a data memory. The storage section 42 may be constituted by a magnetic disk (HD), a semiconductor memory (memory card, SSD), an optical disk, a magneto-optical disk, and the like. The storage section 42 stores various kinds of measurement data acquired from the user terminal 11. The storage section 42 may store a program executed by the processor 41a of the controller 41.

The communication section 43 is a communication interface for communicating with the user terminal 11. The communication section 43 transmits data to the user terminal 11 and receives data from the user terminal 11 via the network. The communications performed by the communication section 43 may be wireless communication or wired communication. In the present embodiment, the communication section 43 will be described as having a configuration for communicating with the user terminal 11 via a network. The communication performed by the communication section 43, however, is not limited to a specific communication scheme.

Next, the functions realized by the controller 21 of the wearable device 2 will be described.

Figure 5:
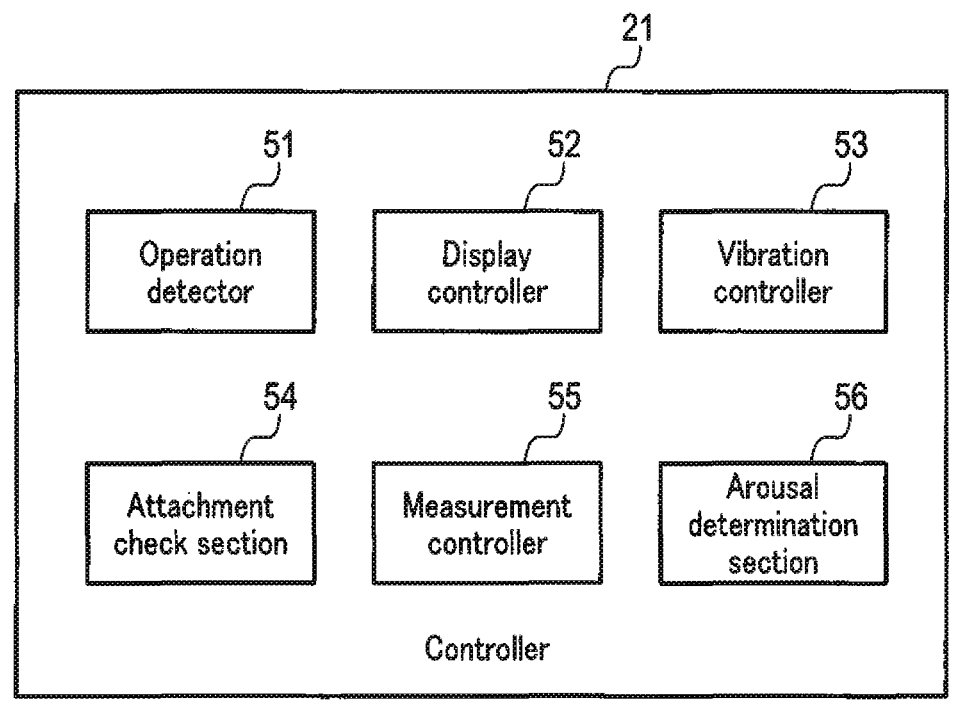
FIG. 5 is a block diagram for explaining functions realized by the controller of the wearable device.

FIG. 5 is a block diagram showing the functions of the controller 21 of the wearable device 2.

The controller 21 of the wearable device 2 realizes various processing functions, with the processor 21a executing the programs stored in the memory 21b. As shown in FIG. 5, the controller 21 of the wearable device 2 includes, as main functions, an operation detector 51, a display controller 52, a vibration controller 53, an attachment check section 54, a measurement controller 55, an arousal determination section 56, and the like.

The operation detector 51 is a function for detecting an operation instruction input by the user (measurement subject) by way of the operation section 35, or an operation instruction input by the user through a specific movement. For example, the controller 21 detects information that is input using the operation section 24, which is a touch panel. The controller 21 also detects a specific movement of the user based on the acceleration data measured by the acceleration sensor 29, and detects an operation instruction corresponding to the detected specific movement.

The display controller 52 is a function for controlling the display contents to be displayed on the display section 25. The controller 21 causes the display controller 52 to display a display screen, which is described later, on the display section 25. In addition, the controller 21 controls the ON/OFF of the display device as the display section 25.

The vibration controller 53 is a function for controlling the vibrations to be generated in the vibrator 26. The controller 21 controls the vibration pattern, the intensity of vibration, and the like, when driving the vibrator 26 by the vibration controller 53 and causing the main body of the wearable device 2 to vibrate.

The attachment check section 54 is a function for checking the attachment state of the CPAP machine 3 that serves as a treatment device. The controller 21 serving as the attachment check section 54 may acquire information indicating the attachment state from the CPAP machine 3 via the user terminal 11, and check the attachment state of the CPAP machine 3 based on the acquired information. In addition, the attachment check section 54 may be configured by arranging electrodes in the mask 3b of the CPAP machine 3 to check whether the CPAP machine 3 is attached to the user, by mutual sensing of the magnetic field electrodes. In addition, the attachment check section 54 may estimate the attachment state of the CPAP machine 3 from blood pressure values that are continuously measured.

The measurement controller 55 is a function for controlling the continuous measurement of the blood pressure value, using the blood pressure sensor 27a. The controller 21 serving as the measurement controller 55 acquires blood pressure data that indicates the blood pressure value continuously measured by the blood pressure sensor 27a (for example, for every beat) and stores it in the storage section 23, or transmits the data to the user terminal 11 or server 12.

The arousal determination section 56 is a function for detecting (determining) the arousal of the user. The arousal determination section 56 may determine (detect) that the measurement subject is in a wakened state by the movement of the measurement subject that is specified from the acceleration data measured by the acceleration sensor 29. The arousal determination section 56 may detect the arousal based on an operation by the measurement subject.

Next, the operation of the treatment system having the above configuration will be described.

The user (measurement subject) operates the wearable device 2 to instruct the continuous measurement (monitoring) of the blood pressure value during sleep, and goes to bed with the CPAP machine 3 on. In response to the monitoring instruction, the wearable device 2 checks the attachment state of the CPAP machine 3. If it is confirmed that the CPAP machine 3 is properly attached, the wearable device 2 begins the continuous measurement of the blood pressure value. If it is not confirmed that the CPAP machine 3 is properly attached, the wearable device 2 prompts the user to check the CPAP machine 3. This prevents monitoring from being conducted during sleep with the CPAP machine 3 unattached.

The wearable device 2 also checks the attachment state of the CPAP machine 3 during sleep (during monitoring). When the detachment of the CPAP machine 3 is detected during sleep (i.e., when it is not confirmed that the CPAP machine 3 is properly attached), the wearable device 2 alerts the user in a manner that ensures he/she will become aware of this even during sleep. This makes it possible to alert the user and prompt him/her to re-attach the CPAP machine 3 when the CPAP machine 3 is not attached during sleep.

Figure 6:
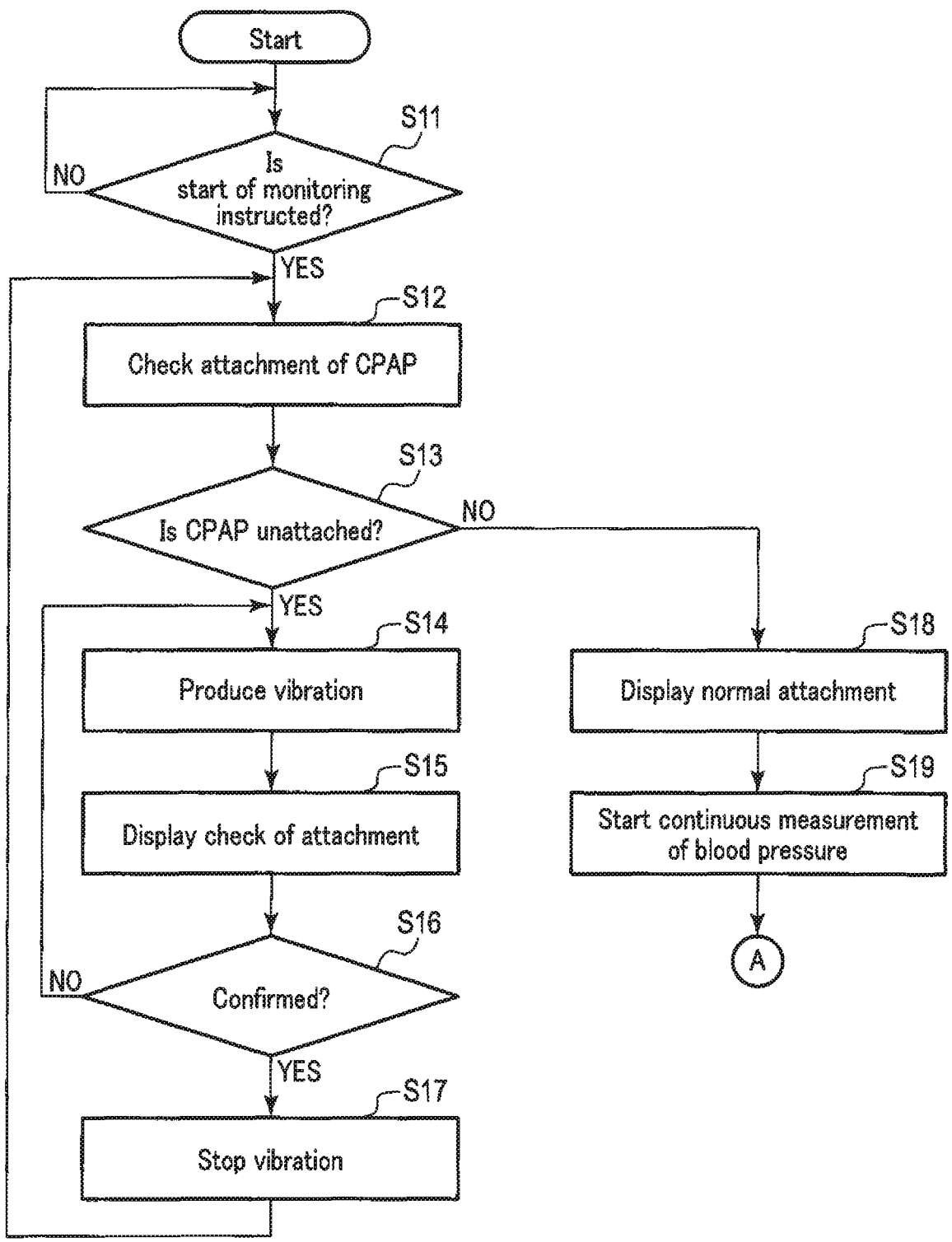
FIG. 6 is a flowchart for explaining an exemplary operation of the wearable device.
Figure 7:
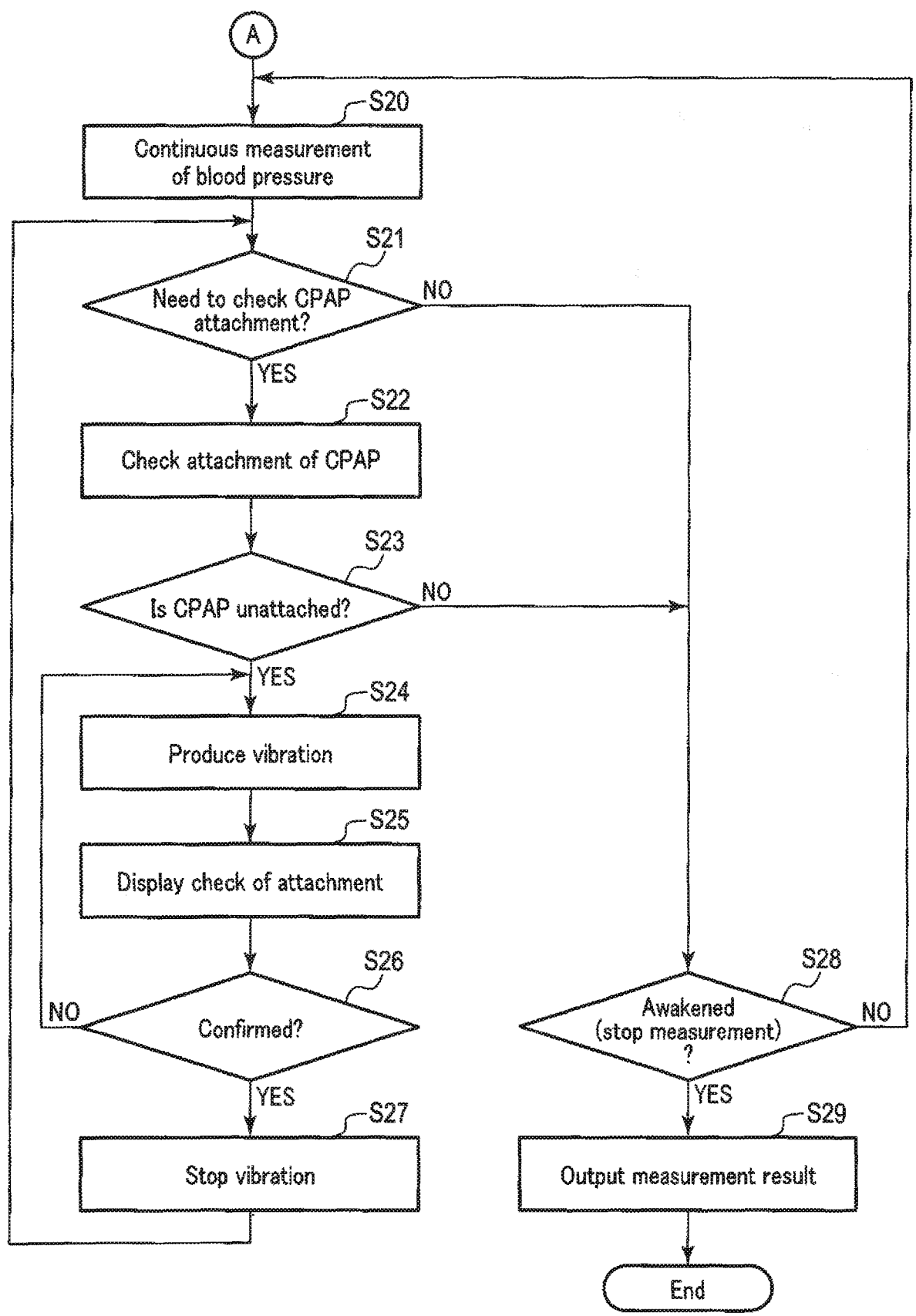
FIG. 7 is a flowchart for explaining an exemplary operation of the wearable device.

FIGS. 6 and 7 are flowcharts that explain an exemplary operation of the wearable device 2 according to the present embodiment.

The user (measurement subject) instructs the continuous measurement (monitoring) of the blood pressure value at bedtime by operating the wearable device 2. The controller 21 of the wearable device 2 receives various operation instructions in accordance with the function of the operation detector 51.

When a monitoring instruction is detected ("YES" at S11), the controller 21 checks the attachment state of the CPAP machine 3 via the function of the attachment check section 54 (S12). For example, the controller 21 may send an inquiry about the attachment state of the CPAP machine 3 to the user terminal 11 to which the CPAP machine 3 is communicably connected. In response, the user terminal 11 notifies the wearable device 2 of a signal indicating the attachment state that is acquired from the CPAP machine 3. Based on the notification result, the controller 21 checks the attachment state of the CPAP machine 3.

The method of checking the attachment state of the CPAP machine 3 is not limited to any specific method. For example, the controller 21 of the wearable device 2 may detect the state of the mask 3b of the CPAP machine 3 being attached to the user through mutual sensing of the magnetic field electrodes. In addition, the user terminal 11 may determine the attachment state of the mask 3b on the user based on the information acquired from the pressure sensor and the flow rate sensor of the CPAP machine 3, and thereby notify the wearable device 2 of the determination result.

If it is determined that the CPAP machine 3 is unattached ("YES" at S12), the controller 21 vibrates the vibrator 26 via the function of the vibration controller 53 to vibrate the body of the wearable device 2 (S14). An alert to check the attachment of the CPAP machine 3 is displayed on the display section 25 via the function of the display controller 52 (S15). After displaying the alert to check the attachment, the controller 21 accepts an indication that the user has confirmed the attachment of the CPAP machine 3 (S16).

When the alert to check the attachment of the CPAP machine 3 is displayed, the user rechecks the attachment of the CPAP machine 3, and, if it is confirmed, the user indicates the completion of the attachment. The controller 21 acquires the indication of the completion of the attachment from the user via the function of the operation detector 51. When an indication that the completion of the attachment has been confirmed is received ("YES" at S16), the controller 21 stops the vibration of the vibrator 26 via the function of the vibration controller 53 (S17), and returns to S12.

When the attachment of the CPAP machine 3 on the user is confirmed ("YES" at S12), the controller 21 displays the confirmed attachment of the CPAP machine 3 on the display section 25 via the function of the display controller 52 (S18). After displaying the confirmed attachment on the display section 25, the controller 21 starts the continuous measurement of the user's blood pressure value with the blood pressure sensor 27a via the function of the measurement controller 55 (S19).

After commencing the continuous measurement of the user's blood pressure value, the controller 21 continues to perform the continuous measurement of the blood pressure value using the blood pressure sensor 27a via the function of the measurement controller 55 (S20). In the continuous measurement of the blood pressure, the controller 21 stores the measured blood pressure values (blood pressure data) of the user in the storage section 23. At the end of the measurement, the controller 21 transfers the blood pressure data collected in the storage section 23 to the user terminal 11 or to the server 12 via the user terminal 11.

The controller 21 may transfer the blood pressure data collected in the storage section 23 to the user terminal 11 or to the server 12 via the user terminal 11 at predetermined intervals. Further, the controller 21 may transfer the blood pressure data to the user terminal 11 or to the server 12 via the user terminal 11, without storing the blood pressure data in the storage section 23. The timing for transferring the blood pressure data to the user terminal 11 or server 12 may be suitably determined in accordance with the storage capacity of the storage section 23 in the wearable device 2, the timing of processing the blood pressure data by the server 12 or user terminal 11, the communication environment, or the like.

During the continuous measurement of the blood pressure, the controller 21 determines whether or not there is a necessity to check the attachment of the CPAP machine 3 (S21). For example, the controller 21 may check the attachment of the CPAP machine 3 at predetermined intervals. If this is the case, the controller 21 checks the attachment of the CPAP machine 3 at every predetermined interval.

The controller 21 may check the attachment of the CPAP machine 3 in accordance with the measured blood pressure data. For example, the controller 21 may check the attachment of the CPAP machine 3 when the measured blood pressure value exceeds a reference value. Alternatively, the controller 21 may check the attachment of the CPAP machine 3 when a change of the blood pressure value that exceeds a reference value is observed.

In addition, the controller 21 may check the attachment of the CPAP machine 3 in accordance with the measurement data other than the blood pressure data. For example, the controller 21 may check the attachment of the CPAP machine 3 in accordance with the movement of the measurement subject (amount of activity or posture change) measured by the acceleration sensor 29. Furthermore, the controller 21 may determine whether or not to check the CPAP machine 3 in accordance with the movement of the measurement subject measured by the acceleration sensor 29 and the blood pressure data in combination.

If it is determined that the attachment of the CPAP machine 3 should be checked ("YES" at S21), the controller 21 checks the attachment of the CPAP machine 3 via the function of the attachment check section 54 (S22). The controller 21 may check the attachment of the CPAP machine 3 in the same manner as S12. For the case of the processing at S22, however, where the continuous measurement of the blood pressure is being executed, the controller 21 may analyze the measured blood pressure data to estimate the attachment state of the CPAP machine 3.

As an estimation based on the analysis of the blood pressure data, the attachment state of the CPAP machine 3 may be estimated from the occurrence of an abrupt blood pressure fluctuation (blood pressure surge) that is extracted from the blood pressure data. The estimation of the attachment state of the CPAP machine 3 based on the analysis of the blood pressure data may be performed by the server 12 or user terminal 11, and the result may be acquired by the wearable device 2. If this is the case, the controller 21 may suitably transfer to the server 12 or the user terminal 11 the blood pressure data that is being continuously measured, and acquire the estimation result based on the transferred blood pressure data.

If it is determined that the CPAP machine 3 is unattached ("YES" at S23) during the continuous measurement (during sleep), the controller 21 drives the vibrator 26 via the function of the vibration controller 53 to vibrate the body of the wearable device 2 (S24). In addition, an alert to check the attachment of the CPAP machine 3 is displayed on the display section 25 by the function of the display controller 52 (S25). For the processing of S24 and S25, an alert may be made to the extent that a sleeping measurement subject will be awakened. In this manner, even if, for example, the mask 3b comes off during sleep, the user can be notified and prompted to reattach the CPAP machine 3.

After displaying the alert to check the attachment, the controller 21 accepts an indication that the measurement subject has confirmed the attachment of the CPAP machine 3 (S26). For example, noticing the alert to check the attachment of the CPAP machine 3, the measurement subject rechecks the attachment of the CPAP machine 3, and indicates, after checking, that the confirmation of the attachment has been completed. The controller 21 detects the indication of the confirmation from the user via the function of the operation detector 51. When the indication of the confirmation by the measurement subject is detected ("YES" at S26), the controller 21 stops the vibration of the vibrator 26 via the function of the vibration controller 53 (S27), and returns to S21.

If the attachment of the CPAP machine 3 is confirmed ("NO" at S23), or if it is determined that the confirmation of the attachment of the CPAP machine 3 is not required ("NO" at S21), the controller 21 continues to perform the continuous measurement of the blood pressure value with the blood pressure sensor 27a via the function of the measurement controller 55. During the continuous measurement of the blood pressure value, the controller 21 detects the arousal of the measurement subject via the function of the arousal determination section 56. The controller 21 may detect that the measurement subject has woken up based on the movement of the measurement subject detected by the acceleration sensor 29. The controller 21 may also detect the arousal in response to an operation by the measurement subject, or may receive an instruction to terminate the blood pressure measurement.

If the arousal of the measurement subject is not detected, or if the termination of the blood pressure measurement is not instructed ("NO" at S28), the controller 21 returns to S20 and continues to perform the continuous measurement of the blood pressure for the measurement subject.

When the arousal of the measurement subject is detected, or when the termination of the blood pressure measurement is instructed ("YES" at S28), the controller 21 transfers the measurement result to the user terminal 11 or server 12 (S29), and terminates the monitoring.

Next, an exemplary display screen displayed on the display section 25 of the wearable device 2 in accordance with the above-described operation will be described.

Figure 8:
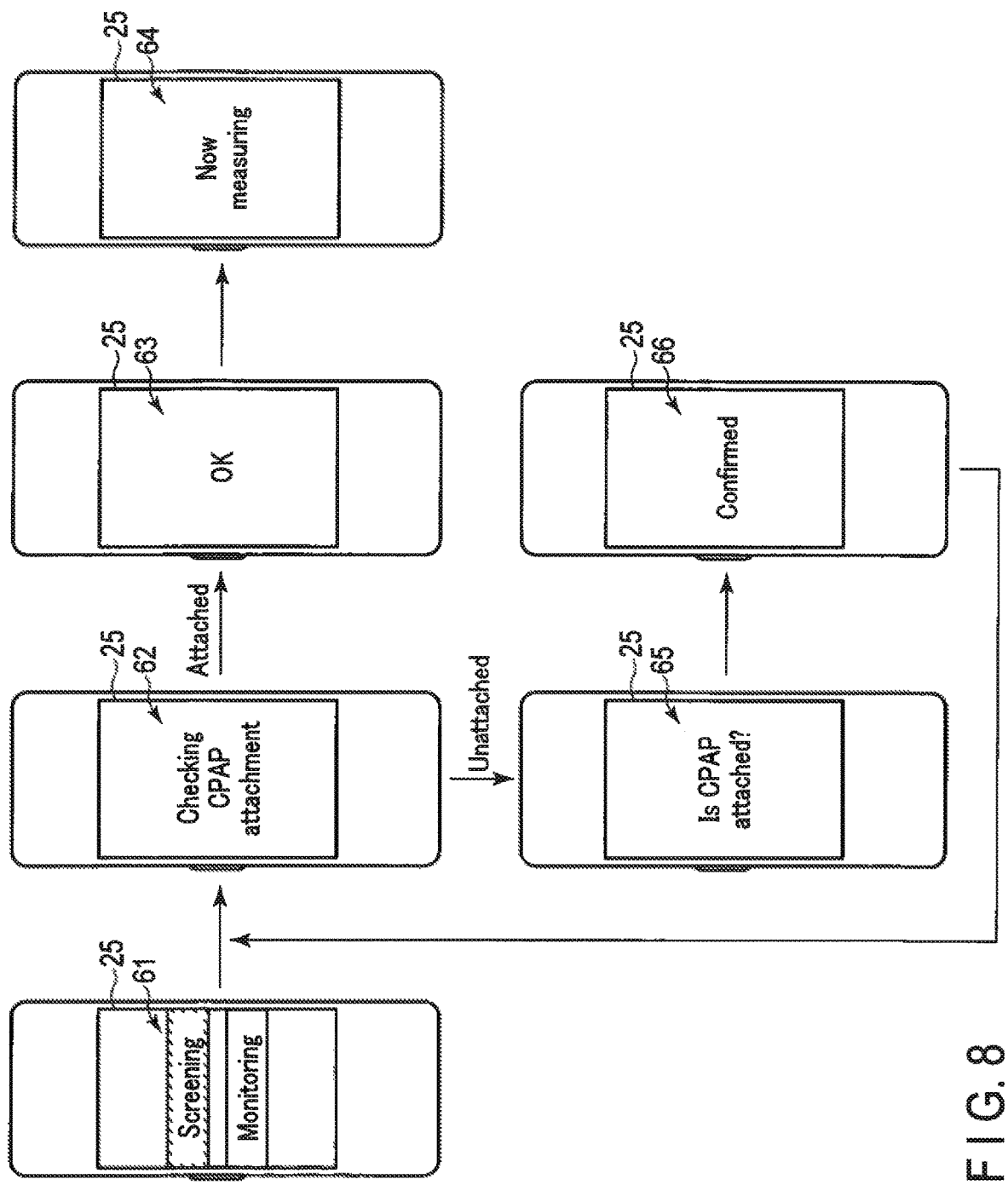
FIG. 8 is a diagram showing an exemplary transition of the display screens displayed by the wearable device.

FIG. 8 is a diagram showing an exemplary transition of the display screens that are displayed by the display section 25 when the wearable device 2 is performing the monitoring.

The display screen 61 shown in FIG. 8 is an exemplary display of an operation screen for indicating an operation mode (screening) in the continuous measurement of the blood pressure. When the user touches "monitoring" on the touch panel that serves as the operation section 24 while the display screen 61 is being displayed, the controller 21 displays the display screen 62 on the display section 25.

The display screen 62 is a screen to notify the user that the attachment of the CPAP machine 3 is being checked. That is, when the monitoring is instructed, the controller 21 checks the attachment of the CPAP machine 3 and displays the display screen 62 on the display section 25 while the attachment is being checked. When the attachment of the CPAP machine 3 is confirmed, the controller 21 displays either a display screen 63 or display screen 65 on the display section 25 in accordance with the result of the attachment check.

The display screen 63 is a screen to notify the user that the attachment of the CPAP machine 3 has been confirmed. That is, when the attachment of the CPAP machine 3 is confirmed, the controller 21 displays on the display section 25 the display screen 63 indicating that the attachment has been confirmed. After displaying the display screen 63, the controller 21 displays a display screen 64 on the display section 25 to indicate that the continuous measurement of the blood pressure is being performed. For example, when the attachment of the CPAP machine 3 is confirmed, the controller 21 may display the display screen 63 on the display section 25 and starts the continuous measurement of the blood pressure. With the display screen 63 being displayed, the controller 21 changes the screen displayed by the display section 25 from the display screen 63 to the display screen 64 in accordance with the user's operation (or movement).

When the CPAP machine 3 is not attached, the display screen 65 serves as a guide screen for urging the user to attach the CPAP machine 3. That is, if the attachment of the CPAP machine 3 is not confirmed, the controller 21 displays on the display section 25 the display screen 65 to prompt the user to check the attachment of the CPAP machine 3.

After displaying the display screen 65, the controller 21 displays a display screen 66 on the display section 25 as an operation screen for prompting the user to confirm the attachment of the CPAP machine 3. When the attachment of the CPAP machine 3 is confirmed on the display screen 66, the controller 21 displays the display screen 62 on the display section 25 to check the attachment of the CPAP machine 3 again.

Figure 9:
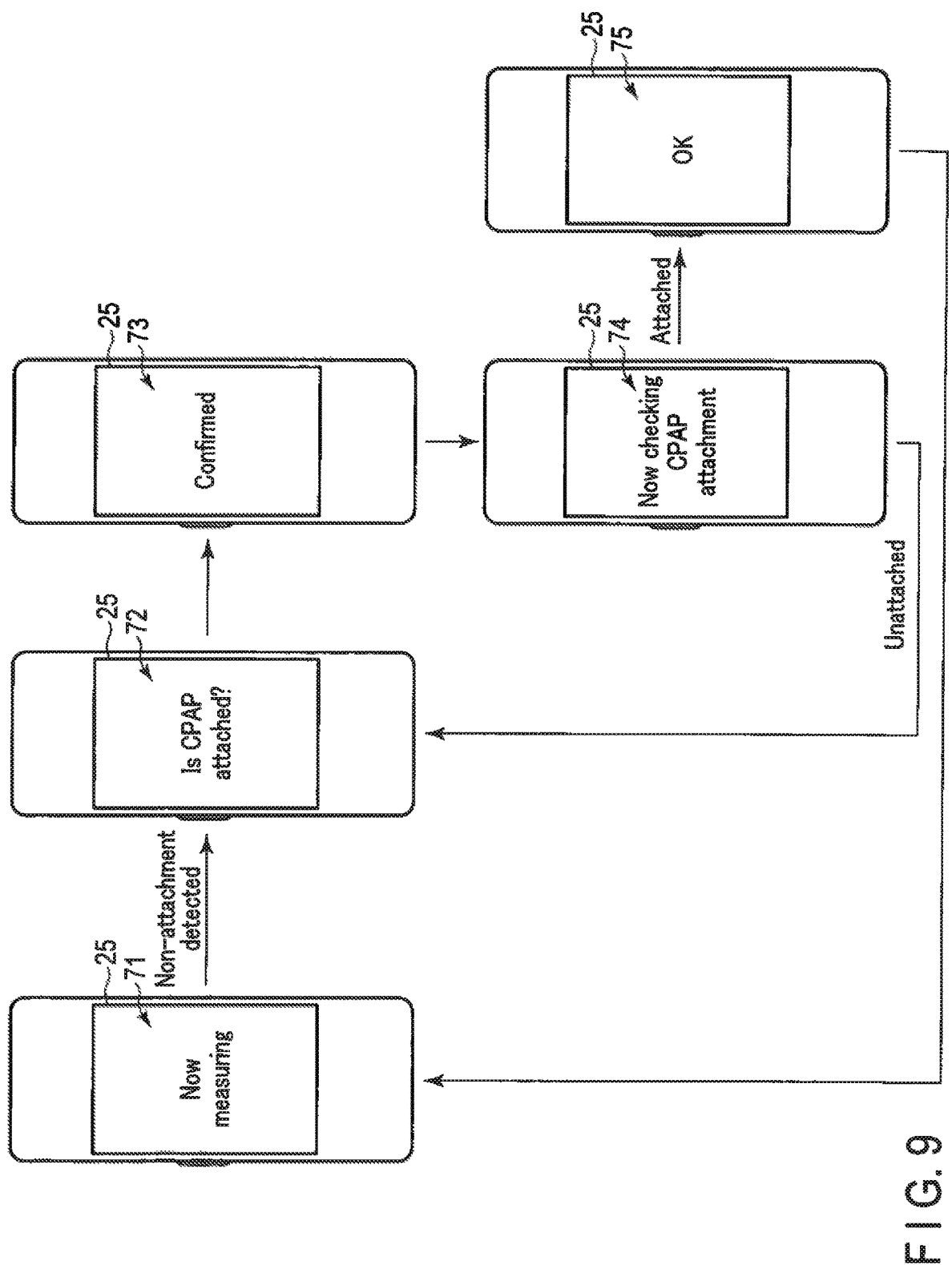
FIG. 9 is a diagram showing an exemplary transition of the display screens displayed by the wearable device.

FIG. 9 is a diagram showing an exemplary transition of the display screens that are displayed by the display section 25 when the wearable device 2 is performing the monitoring.

A display screen 71 shown in FIG. 9 is an exemplary display of a guidance screen indicating that the continuous measurement of the blood pressure (monitoring) is being performed. When a specific event occurs such as the start of measurement, the controller 21 displays the display screen 71 for a predetermined length of time, and turns the display screen 71 off after displaying it for the predetermined length of time. In this manner, the wearable device 2 can prevent the user's sleep from being hindered by the display screen 71 displayed at bedtime, and can reduce the battery consumption.

In a manner similar to the display screen 65, the display screen 72 is displayed when the CPAP machine 3 being unattached is detected. That is, if the controller 21 detects during monitoring that the CPAP machine 3 is not attached, the controller 21 displays the display screen 72 on the display section 25 and issues an alert to check the attachment of the CPAP machine 3. After displaying the display screen 72, the controller 21 displays a display screen 73 on the display section 25, as an operation screen for prompting the user to confirm the attachment of the CPAP machine 3. When it is indicated that the attachment of the CPAP machine 3 is confirmed, the controller 21 displays the display screen 74 on the display section 25 to check the attachment of the CPAP machine 3.

When checking the attachment of the CPAP machine 3 after the completion of the confirmation is indicated by the user, the controller 21 displays a display screen 74 on the display section 25 to indicate that the attachment is being checked. The display content of the display screen 74 may be similar to the display content of the display screen 65. If the attachment of the CPAP machine 3 is confirmed when the display screen 74 is displayed, the controller 21 displays a display screen 75 on the display section 25 to indicate that the attachment of the CPAP machine 3 is confirmed. After displaying the display screen 75, the controller 21 continues to measure the blood pressure. The controller 21 may turn off the display screen 75 after a predetermined length of time has elapsed. If the attachment of the CPAP machine 3 is not confirmed, the controller 21 displays the display screen 72 again on the display section 25, and prompts the user to confirm the attachment again.

As described above, when the start of the continuous measurement of the blood pressure is instructed, the wearable device according to the present embodiment is configured to check whether the CPAP machine is attached to the measurement subject, and if it is confirmed that the CPAP machine is attached, the continuous measurement of the blood pressure is performed, while if the attachment of the CPAP machine is not confirmed, an alert that prompts the user to attach the CPAP machine is issued. In this manner, the wearable device according to the present embodiment can check whether the CPAP machine is attached when commencing the continuous measurement of the blood pressure, and can realize the continuous measurement of the blood pressure with the CPAP machine securely attached.

Furthermore, the wearable device according to the present embodiment checks whether the CPAP machine is attached even during the continuous measurement of the blood pressure, and if the CPAP machine not being attached is detected during the measurement, the wearable device issues an alert and prompts the attachment of the CPAP machine. The wearable device according to the present embodiment can therefore notify the measurement subject that the CPAP machine has come off during the continuous measurement of the blood pressure.

The present invention is not limited to the above-described embodiment as is, and can be embodied by modifying the structural components without departing from the scope of the invention at the implementation stage. Furthermore, various inventions can be produced by suitably combining structural components disclosed in the embodiment. For example, some components may be omitted from the entire set of structural components shown in the embodiment. Furthermore, the structural components of different embodiments may be suitably combined.

Part of the above embodiment, or the entire embodiment, may be described as in the following notes, but not limited thereto.

(Note 1)
A wearable device including:
a memory; and
at least one processor that cooperates with the memory, wherein the processor is configured to:
detect an instruction for commencing a continuous measurement of blood pressure with a blood pressure sensor that continuously measures blood pressure of a measurement subject;
when the instruction for commencing the continuous measurement of the blood pressure is detected, check whether a treatment device to be used during the continuous measurement of the blood pressure is attached to the measurement subject;
when it is confirmed that the treatment device is attached, execute the continuous measurement of the blood pressure; and
when it is not confirmed that the treatment device is attached, display a form of guidance to prompt attachment of the treatment device.

The invention claimed is:

1. A wearable device comprising:
a blood pressure sensor configured to continuously measure blood pressure of a measurement subject;
a check section configured to, in response to an instruction for commencing a continuous measurement of the blood pressure, check, before commencing a continuous measurement of the blood pressure, whether a treatment device that is to be used during the continuous measurement of the blood pressure is attached to the measurement subject, and check, during the continuous measurement of the blood pressure, whether the treatment device is attached;
a measurement controller configured to, when the check section confirms that the treatment device is attached before commencing the continuous measurement of the blood pressure, execute a continuous measurement of the blood pressure with the blood pressure sensor;
a display section configured to, when the check section does not confirm that the treatment device is attached before commencing the continuous measurement of the blood pressure, display a form of guidance to prompt attachment of the treatment device; and
a vibrator configured to, when the attachment of the treatment device is not confirmed during the continuous measurement of the blood pressure, vibrate a main body of the wearable device.

2. The wearable device according to claim 1, wherein the treatment device is a continuous positive airway pressure (CPAP) machine.

3. The wearable device according to claim 2, wherein the vibrator is configured to vibrate the main body when the attachment of the treatment device is not confirmed by the check section before starting the continuous measurement of the blood pressure.

4. The wearable device according to claim 2, wherein, when the measurement controller satisfies a predetermined condition during the continuous measurement of the blood pressure of the measurement subject, the check section checks whether the treatment device is attached to the measurement subject.

5. The wearable device according to claim 2, wherein the blood pressure sensor includes a blood pressure sensor of a pulse transmit time (PTT) system, a tonometry system, an optical system, a radio wave system, or an ultrasonic system.

6. The wearable device according to claim 2, comprising:
a display controller configured to, when the attachment of the treatment device is not confirmed during the continuous measurement of the blood pressure, issue an alert to prompt the attachment of the treatment device.

7. The wearable device according to claim 1, wherein the vibrator is configured to vibrate the main body when the check section does not confirm that the treatment device is attached before commencing the continuous measurement of the blood pressure.

8. The wearable device according to claim 7, wherein, when the measurement controller satisfies a predetermined condition during the continuous measurement of the blood pressure of the measurement subject, the check section checks whether the treatment device is attached to the measurement subject.

9. The wearable device according to claim 7, wherein the blood pressure sensor includes a blood pressure sensor of a pulse transmit time (PTT) system, a tonometry system, an optical system, a radio wave system, or an ultrasonic system.

10. The wearable device according to claim 7, comprising:
a display controller configured to, when the attachment of the treatment device is not confirmed during the continuous measurement of the blood pressure, issue an alert to prompt the attachment of the treatment device.

11. The wearable device according to claim 1, wherein, when the measurement controller satisfies a predetermined condition during the continuous measurement of the blood pressure of the measurement subject, the check section checks whether the treatment device is attached to the measurement subject.

12. The wearable device according to claim 11, wherein the blood pressure sensor includes a blood pressure sensor of a pulse transmit time (PTT) system, a tonometry system, an optical system, a radio wave system, or an ultrasonic system.

13. The wearable device according to claim 1, wherein the blood pressure sensor includes a blood pressure sensor of a pulse transmit time (PTT) system, a tonometry system, an optical system, a radio wave system, or an ultrasonic system.

14. The wearable device according to claim 1, comprising:
   a display controller configured to, when the attachment of the treatment device is not confirmed during the continuous measurement of the blood pressure, issue an alert to prompt the attachment of the treatment device.

15. A non-transitory computer-readable storage medium storing a program that causes a processor of a wearable device, which comprises a display section and a blood pressure sensor configured to continuously measure blood pressure of a measurement subject, to implement functions of:
   in response to an instruction of commencing the continuous measurement of the blood pressure, checking, before commencing the continuous measurement of the blood pressure, whether a treatment device that is to be used during the continuous measurement of the blood pressure is attached to the measurement subject, and checking, during the continuous measurement of the blood pressure, whether the treatment device is attached;
   when the attachment of the treatment device is confirmed before commencing the continuous measurement of the blood pressure, executing the continuous measurement of the blood pressure with the blood pressure sensor;
   when the attachment of the treatment device is not confirmed before commencing the continuous measurement of the blood pressure, displaying a form of guidance on the display section to prompt attachment of the treatment device; and
   when the attachment of the treatment device is not confirmed before commencing the continuous measurement of the blood pressure, vibrating a main body.

* * * * *